(12) United States Patent
Graepel et al.

(10) Patent No.: US 10,867,242 B2
(45) Date of Patent: Dec. 15, 2020

(54) SELECTING ACTIONS TO BE PERFORMED BY A REINFORCEMENT LEARNING AGENT USING TREE SEARCH

(71) Applicant: DeepMind Technologies Limited, London (GB)

(72) Inventors: Thore Kurt Hartwig Graepel, Cambridge (GB); Shih-Chieh Huang, London (GB); David Silver, Hitchin (GB); Arthur Clement Guez, London (GB); Laurent Sifre, Paris (FR); Ilya Sutskever, San Francisco, CA (US); Christopher Maddison, Toronto (CA)

(73) Assignee: DeepMind Technologies Limited, Mountain View, CA (US)

( * ) Notice: Subject to any disclaimer, the term of this patent is extended or adjusted under 35 U.S.C. 154(b) by 630 days.

(21) Appl. No.: 15/280,784

(22) Filed: Sep. 29, 2016

(65) Prior Publication Data

US 2018/0032864 A1    Feb. 1, 2018

(30) Foreign Application Priority Data

Jul. 27, 2016    (DE) .................... 20 2016 004 628 U (51) Int. Cl.
*G06N 3/08*    (2006.01)
*G06N 3/04*    (2006.01)
(Continued)

(52) U.S. Cl.
CPC ........... *G06N 3/08* (2013.01); *G06F 16/9027* (2019.01); *G06N 3/0427* (2013.01);
(Continued)

(58) Field of Classification Search
CPC ...... G06N 3/08; G06N 3/0427; G06N 3/0454; G06N 5/003; G06N 20/00; G06F 16/9027
See application file for complete search history.

(56) References Cited

U.S. PATENT DOCUMENTS 10,124,488 B2 * 11/2018 Lee .................... B25J 9/1666
10,509,918 B1 * 12/2019 Cho .................... G06F 21/6227
(Continued)

OTHER PUBLICATIONS

O.D. Karaduman, "Intelligent 'Health Restoration System': Reinforcement Learning Feedback to Diagnosis and Treatment Planning," in Proceedings of the 5th WESAS Intl. Conf. on Telecomm. and Informatics, Istanbul Turkey, May 27-29, 2006, pp. 436-468 (Year: 2006).*

(Continued)

*Primary Examiner* — Eric Nilsson
*Assistant Examiner* — Urmana Islam
(74) *Attorney, Agent, or Firm* — Fish & Richardson P.C.

(57) ABSTRACT

Methods, systems and apparatus, including computer programs encoded on computer storage media, for training a value neural network that is configured to receive an observation characterizing a state of an environment being interacted with by an agent and to process the observation in accordance with parameters of the value neural network to generate a value score. One of the systems performs operations that include training a supervised learning policy neural network; initializing initial values of parameters of a reinforcement learning policy neural network having a same architecture as the supervised learning policy network to the trained values of the parameters of the supervised learning policy neural network; training the reinforcement learning policy neural network on second training data; and training the value neural network to generate a value score for the state of the environment that represents a predicted long-term reward resulting from the environment being in the state.

21 Claims, 4 Drawing Sheets

(51) Int. Cl.
G06N 5/00 (2006.01)
G06N 20/00 (2019.01)
G06F 16/90 (2019.01)
G16H 50/20 (2018.01)
G16B 40/00 (2019.01)
G06F 16/901 (2019.01)

(52) U.S. Cl.
CPC ........... *G06N 3/0454* (2013.01); *G06N 5/003* (2013.01); *G16B 40/00* (2019.02); *G16H 50/20* (2018.01)

(56) References Cited

U.S. PATENT DOCUMENTS

2015/0094850 A1* 4/2015 Passot ............... B25J 9/163
700/245
2017/0364829 A1* 12/2017 Fyffe ................. G06N 3/006

OTHER PUBLICATIONS

Gabriela Czibula, Maria-Iuliana Bocicor and Istvan-Gergely Czibula, "A Reinforcement Learning Model for Solving the Folding Problem" in Intl. J. Comp. Tech. Appl., vol. 2, pp. 171-181 (2011) (Year: 2011).*
Christopher D. Rosin, "Nested Rollout Policy Adaptation for Monte Carlo Tree Search" in Proceedings of the Twenty-Second Intl. Joint Conf. on Art. Intel., Barcelona, Spain, Jul. 19-22, 2011, pp. 649-654 (Year: 2011).*
Yuandong Tian, Yan Zhu, "Better Computer Go Player With Neural Network and Long-Term Prediction" in International Conference on Learning Representations 2016, Feb. 29, 2016, pp. 1-10 (Year: 2016).*
Van den Dries, Sjoerd, and Marco A. Wiering. "Neural-fitted TD-leaf learning for playing Othello with structured neural networks." IEEE Transactions on Neural Networks and Learning Systems 23, No. 11 (2012): 1701-1713. (Year: 2012).*
Silver et al. "Mastering the game of Go with deep neural networks and tree search," Nature, 2016, 529.7587, pp. 484-489.
Van den Herik et al "Games solved: now and in the future," Artif. Intell. 134, 2002, 277-311.
Campbell et al. "Deep Blue," Artif. Intell. 134, 2002, pp. 57-83.
Schaeffer et al. "A world championship caliber checkers program," Artif. Intell. 53, 1992, 19 pages.
Buro. "From simple features to sophisticated evaluation functions," In 1st International Conference on Computers and Games, 1998, 20 pages.
Müller. "Computer Go," Artif. Intell. 134, 2002, pp. 145-179.
Tesauro et al. "On-line policy improvement using Monte-Carlo Search," In Advances in Neural Information Processing, 1996, 7 pages.
Sheppard. "World-championship-caliber Scrabble," Artif. Intell. 134, 2002, 241-275.
Bouzy et al. "Monte-Carlo Go developments," In 10th International Conference on Advances in Computer Games, 2003, pp. 159-174.
Coulom. "Efficient selectivity and backup operators in Monte-Carlo treesearch." In 5th International Conference on Computers and Games, 2006, 72-83.

Kocsis et al. "Bandit based Monte-Carlo planning," In 15th European Conference on Machine Learning, 2006, 12 pages.
Coulom. "Computing Elo ratings of move patterns in the game of Go," ICGA J. 30, 2007, 13 pages.
Baudiš et al. "Pachi: State of the art open source Go program," In Advances in Computer Games, 2012, pp. 24-38.
Müller et al. "Fuego—an open-source framework for board games and Go engine based on Monte-Carlo tree search," IEEE Trans. Comput. Intell. AI in Games 2, 2010, pp. 259-270.
Gelly et al. "Combining online and offline learning in UCT," In 17th International Conference on Machine Learning,2007, 8 pages.
Krizhevsky et al. "ImageNet classification with deep convolutional neural networks," In Advances in Neural Information Processing Systems, 2012, 9 pages.
Lawrence et al. "Face recognition: a convolutional neural-network approach," IEEE Trans. Neural Netw. 8, 1997, 16 pages.
Mnih et al. "Human-level control through deep reinforcement learning," Nature 518, 2015,13 pages.
LeCun et al. "Deep learning," Nature 521, 2015, 35 pages.
Stern et al. "Bayesian pattern ranking for move prediction in the game of Go," In International Conference of Machine Learning, 2006, 873-880.
Sutskever et al. "Mimicking Go experts with convolutional neural Networks," In International Conference on Artificial Neural Networks, 2008, 101-110.
Maddison et al. "Move evaluation in Go using deep convolutional neural networks," 3rd International Conference on Learning Representations, 2015, 8 pages.
Clark et al. "Training deep convolutional neural networks to play go," In 32nd International Conference on Machine Learning, 2015, 9 pages.
Williams. "Simple statistical gradient-following algorithms for connectionist reinforcement learning," Mach. Learn. 8, 1992, 28 pages.
Sutton et al. "Policy gradient methods for reinforcement learning with function approximation," In Advances in Neural Information Processing Systems, 1999, 7 pages.
Schraudolph et al. "Temporal difference learning of position evaluation in the game of Go," Adv. Neural Inf. Process. Syst. 6, 1994, 8 pages.
Enzenberger. "Evaluation in Go by a neural network using soft segmentation," In 10th Advances in Computer Games Conference, 2003, 12 pages.
Silver et al. "Temporal-difference search in computer Go," Mach. Learn. 87, 2012, 2 pages.
Levinovitz. "The mystery of Go, the ancient game that computers still can't win," Wired Magazine, 2014, 13 pages.
Mechner. "All Systems Go," The Sciences 38, 1998, 14 pages.
Mandziuk. "Computational intelligence in mind games," In Challenges for Computational Intelligence, 2007, 37 pages.
Browne et al. "A survey of Monte-Carlo tree search methods," IEEE Trans. Comput. Intell. AI in Games 4, 2012, 49 pages.
Gelly et al. "The grand challenge of computer Go: Monte Carlo tree search and extensions," Commun. ACM 55, 2012, pp. 10 pages.
Coulom. "Whole-history rating: A Bayesian rating system for players of time-varying strength," In International Conference on Computers and Games, 2008, pp. 13 pages.
'Gokgs.com' [online]. "Rating System Math," Dec. 2016, [retrieved on Dec. 28, 2016] Retrieved from Internet: URL<http://www.gokgs.com/help/rmath.html> 3 pages.

* cited by examiner

SELECTING ACTIONS TO BE PERFORMED BY A REINFORCEMENT LEARNING AGENT USING TREE SEARCH

CROSS-REFERENCE TO RELATED APPLICATION

This application claims the benefit of priority to German Utility Model Application No. 20 2016 004 628.5, filed on Jul. 27, 2016, the entire contents of which are incorporated herein by reference.

BACKGROUND

This specification relates to selecting actions to be performed by a reinforcement learning agent.

Reinforcement learning agents interact with an environment by receiving an observation that characterizes the current state of the environment, and in response, performing an action. Once the action is performed, the agent receives a reward that is dependent on the effect of the performance of the action on the environment.

Some reinforcement learning systems use neural networks to select the action to be performed by the agent in response to receiving any given observation.

Neural networks are machine learning models that employ one or more layers of nonlinear units to predict an output for a received input. Some neural networks are deep neural networks that include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

SUMMARY

This specification describes technologies that relate to reinforcement learning.

The subject matter described in this specification can be implemented in particular embodiments so as to realize one or more of the following advantages. Actions to be performed by an agent interacting with an environment that has a very large state space can be effectively selected to maximize the rewards resulting from the performance of the action. In particular, actions can effectively be selected even when the environment has a state tree that is too large to be exhaustively searched. By using neural networks in searching the state tree, the amount of computing resources and the time required to effectively select an action to be performed by the agent can be reduced. Additionally, neural networks can be used to reduce the effective breadth and depth of the state tree during the search, reducing the computing resources required to search the tree and to select an action. By employing a training pipeline for training the neural networks as described in this specification, various kinds of training data can be effectively utilized in the training, resulting in trained neural networks with better performance.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification generally describes a reinforcement learning system that selects actions to be performed by a reinforcement learning agent interacting with an environment. In order to interact with the environment, the reinforcement learning system receives data characterizing the current state of the environment and selects an action to be performed by the agent from a set of actions in response to the received data. Once the action has been selected by the reinforcement learning system, the agent performs the action to interact with the environment.

Generally, the agent interacts with the environment in order to complete one or more objectives and the reinforcement learning system selects actions in order to maximize the objectives, as represented by numeric rewards received by the reinforcement learning system in response to actions performed by the agent.

In some implementations, the environment is a real-world environment and the agent is a control system for a mechanical agent interacting with the real-world environment. For example, the agent may be a control system integrated in an autonomous or semi-autonomous vehicle navigating through the environment. In these implementations, the actions may be possible control inputs to control the vehicle and the objectives that the agent is attempting to complete are objectives for the navigation of the vehicle through the real-world environment. For example, the objectives can include one or more of: reaching a destination, ensuring the safety of any occupants of the vehicle, minimizing energy used in reaching the destination, maximizing the comfort of the occupants, and so on.

In some other implementations, the environment is a real-world environment and the agent is a computer system that generates outputs for presentation to a user.

For example, the environment may be a patient diagnosis environment such that each state is a respective patient state of a patient, i.e., as reflected by health data characterizing the health of the patient, and the agent may be a computer system for suggesting treatment for the patient. In this example, the actions in the set of actions are possible medical treatments for the patient and the objectives can include one or more of maintaining a current health of the patient, improving the current health of the patient, minimizing medical expenses for the patient, and so on.

As another example, the environment may be a protein folding environment such that each state is a respective state of a protein chain and the agent is a computer system for determining how to fold the protein chain. In this example, the actions are possible folding actions for folding the protein chain and the objective may include, e.g., folding the protein so that the protein is stable and so that it achieves a particular biological function. As another example, the agent may be a mechanical agent that performs the protein folding actions selected by the system automatically without human interaction.

In some other implementations, the environment is a simulated environment and the agent is implemented as one or more computer programs interacting with the simulated environment. For example, the simulated environment may be a virtual environment in which a user competes against a computerized agent to accomplish a goal and the agent is the computerized agent. In this example, the actions in the set of actions are possible actions that can be performed by the computerized agent and the objective may be, e.g., to win the competition against the user.

Figure 1:
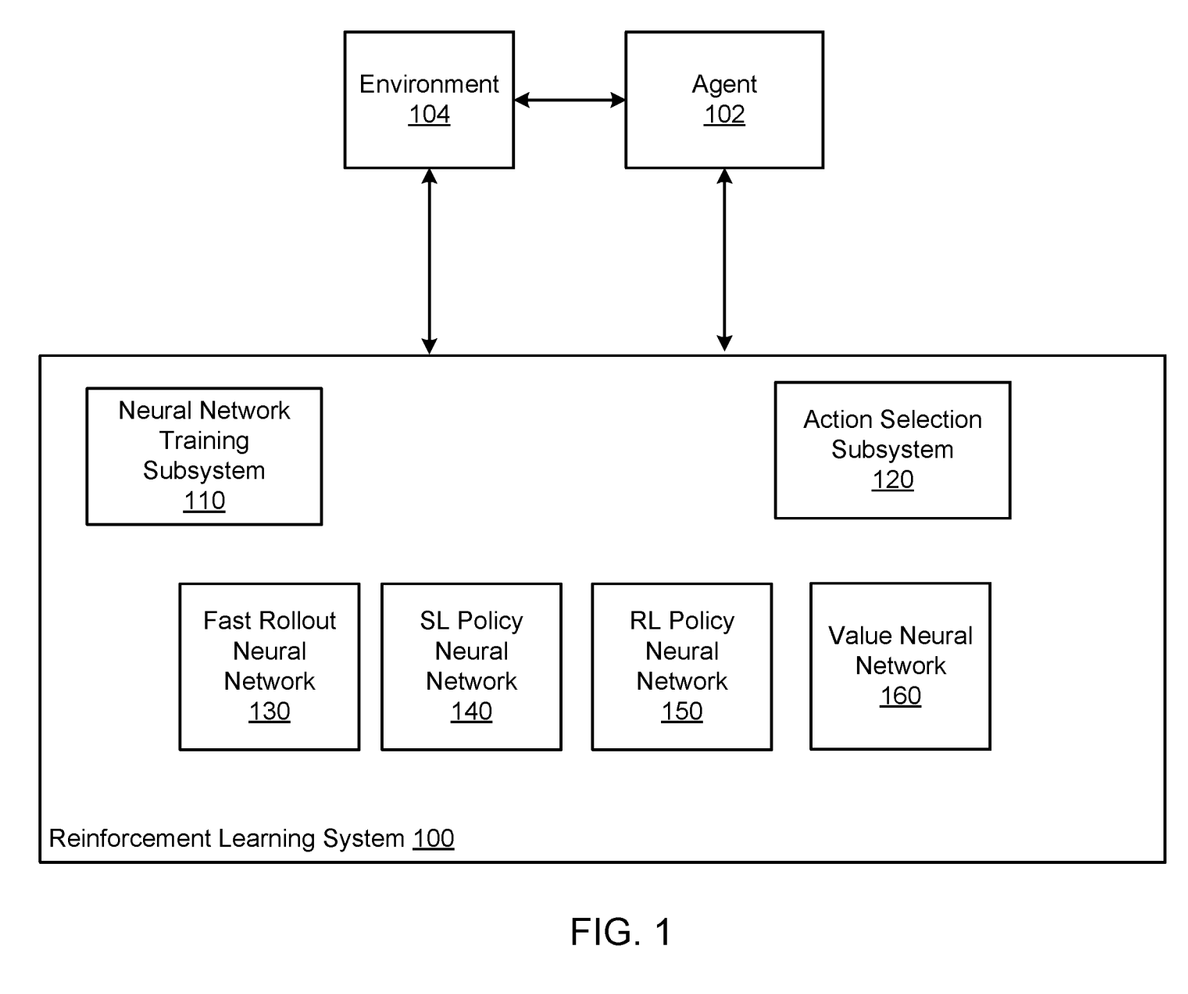
FIG. 1 shows an example reinforcement learning system.

FIG. 1 shows an example reinforcement learning system 100. The reinforcement learning system 100 is an example of a system implemented as computer programs on one or more computers in one or more locations in which the systems, components, and techniques described below are implemented.

The reinforcement learning system 100 selects actions to be performed by a reinforcement learning agent 102 interacting with an environment 104. That is, the reinforcement learning system 100 receives observations, with each observation being data characterizing a respective state of the environment 104, and, in response to each received observation, selects an action from a set of actions to be performed by the reinforcement learning agent 102 in response to the observation.

Once the reinforcement learning system 100 selects an action to be performed by the agent 102, the reinforcement learning system 100 instructs the agent 102 and the agent 102 performs the selected action. Generally, the agent 102 performing the selected action results in the environment 104 transitioning into a different state.

The observations characterize the state of the environment in a manner that is appropriate for the context of use for the reinforcement learning system 100.

For example, when the agent 102 is a control system for a mechanical agent interacting with the real-world environment, the observations may be images captured by sensors of the mechanical agent as it interacts with the real-world environment and, optionally, other sensor data captured by the sensors of the agent.

As another example, when the environment 104 is a patient diagnosis environment, the observations may be data from an electronic medical record of a current patient.

As another example, when the environment 104 is a protein folding environment, the observations may be images of the current configuration of a protein chain, a vector characterizing the composition of the protein chain, or both.

In particular, the reinforcement learning system 100 selects actions using a collection of neural networks that includes at least one policy neural network, e.g., a supervised learning (SL) policy neural network 140, a reinforcement learning (RL) policy neural network 150, or both, a value neural network 160, and, optionally, a fast rollout neural network 130.

Generally, a policy neural network is a neural network that is configured to receive an observation and to process the observation in accordance with parameters of the policy neural network to generate a respective action probability for each action in the set of possible actions that can be performed by the agent to interact with the environment.

In particular, the SL policy neural network 140 is a neural network that is configured to receive an observation and to process the observation in accordance with parameters of the supervised learning policy neural network 140 to generate a respective action probability for each action in the set of possible actions that can be performed by the agent to interact with the environment.

When used by the reinforcement learning system 100, the fast rollout neural network 130 is also configured to generate action probabilities for actions in the set of possible actions (when generated by the fast rollout neural network 130, these probabilities will be referred to in this specification as "rollout action probabilities"), but is configured to generate an output faster than the SL policy neural network 140.

That is, the processing time necessary for the fast rollout policy neural network 130 to generate rollout action probabilities is less than the processing time necessary for the SL policy neural network 140 to generate action probabilities.

To that end, the fast rollout neural network 130 is a neural network that has an architecture that is more compact than the architecture of the SL policy neural network 140 and the inputs to the fast rollout policy neural network (referred to in this specification as "rollout inputs") are less complex than the observations that are inputs to the SL policy neural network 140.

For example, in implementations where the observations are images, the SL policy neural network 140 may be a convolutional neural network configured to process the images while the fast rollout neural network 130 is a shallower, fully-connected neural network that is configured to receive as input feature vectors that characterize the state of the environment 104.

The RL policy neural network 150 is a neural network that has the same neural network architecture as the SL policy neural network 140 and therefore generates the same kind of output. However, as will be described in more detail below, in implementations where the system 100 uses both the RL policy neural network and the SL policy neural network, because the RL policy neural network 150 is trained differently from the SL policy neural network 140, once both neural networks are trained, parameter values differ between the two neural networks.

The value neural network 160 is a neural network that is configured to receive an observation and to process the observation to generate a value score for the state of the environment characterized by the observation. Generally, the value neural network 160 has a neural network architecture that is similar to that of the SL policy neural network 140 and the RL policy neural network 150 but has a different type of output layer from that of the SL policy neural network 140 and the RL policy neural network 150, e.g., a regression output layer, that results in the output of the value neural network 160 being a single value score.

To allow the agent 102 to effectively interact with the environment 104, the reinforcement learning system 100 includes a neural network training subsystem 110 that trains the neural networks in the collection to determine trained values of the parameters of the neural networks.

When used by the system 100 in selecting actions, the neural network training subsystem 110 trains the fast rollout neural network 130 and the SL policy neural network 140 on labeled training data using supervised learning and trains the RL policy neural network 150 and the value neural network 160 based on interactions of the agent 102 with a simulated version of the environment 104.

Generally, the simulated version of the environment 104 is a virtualized environment that simulates how actions performed by the agent 120 would affect the state of the environment 104.

For example, when the environment 104 is a real-world environment and the agent is an autonomous or semi-autonomous vehicle, the simulated version of the environment is a motion simulation environment that simulates navigation through the real-world environment. That is, the motion simulation environment simulates the effects of various control inputs on the navigation of the vehicle through the real-world environment.

As another example, when the environment 104 is a patient diagnosis environment, the simulated version of the environment is a patient health simulation that simulates effects of medical treatments on patients. For example, the patient health simulation may be a computer program that receives patient information and a treatment to be applied to the patient and outputs the effect of the treatment on the patient's health.

As another example, when the environment 104 is a protein folding environment, the simulated version of the environment is a simulated protein folding environment that simulates effects of folding actions on protein chains. That is, the simulated protein folding environment may be a computer program that maintains a virtual representation of a protein chain and models how performing various folding actions will influence the protein chain.

As another example, when the environment 104 is the virtual environment described above, the simulated version of the environment is a simulation in which the user is replaced by another computerized agent.

Training the collection of neural networks is described in more detail below with reference to FIG. 2.

The reinforcement learning system 100 also includes an action selection subsystem 120 that, once the neural networks in the collection have been trained, uses the trained neural networks to select actions to be performed by the agent 102 in response to a given observation.

In particular, the action selection subsystem 120 maintains data representing a state tree of the environment 104. The state tree includes nodes that represent states of the environment 104 and directed edges that connect nodes in the tree. An outgoing edge from a first node to a second node in the tree represents an action that was performed in response to an observation characterizing the first state and resulted in the environment transitioning into the second state.

While the data is logically described as a tree, the action selection subsystem 120 can be represented by any of a variety of convenient physical data structures, e.g., as multiple triples or as an adjacency list.

The action selection subsystem 120 also maintains edge data for each edge in the state tree that includes (i) an action score for the action represented by the edge, (ii) a visit count for the action represented by the edge, and (iii) a prior probability for the action represented by the edge.

At any given time, the action score for an action represents the current likelihood that the agent 102 will complete the objectives if the action is performed, the visit count for the action is the current number of times that the action has been performed by the agent 102 in response to observations characterizing the respective first state represented by the respective first node for the edge, and the prior probability represents the likelihood that the action is the action that should be performed in response to observations characterizing the respective first state as determined by the output of one of the neural networks, and not as determined by subsequent interactions of the agent 102 with the environment 104 or the simulated version of the environment 104.

The action selection subsystem 120 updates the data representing the state tree and the edge data for the edges in the state tree from interactions of the agent 102 with the simulated version of the environment 104 using the trained neural networks in the collection. In particular, the action selection subsystem 120 repeatedly performs searches of the state tree to update the tree and edge data. Performing a search of the state tree to update the state tree and the edge data is described in more detail below with reference to FIG. 4.

In some implementations, the action selection subsystem 120 performs a specified number of searches or performs searches for a specified period of time to finalize the state tree and then uses the finalized state tree to select actions to be performed by the agent 102 in interacting with the actual environment 104, i.e., and not the simulated version of the environment.

In other implementations, however, the action selection subsystem 120 continues to update the state tree by performing searches as the agent 102 interacts with the actual environment 104, i.e., as the agent 102 continues to interact with the environment 104, the action selection subsystem 120 continues to update the state tree.

In any of these implementations, however, when an observation is received by the reinforcement learning system 100, the action selection subsystem 120 selects the action to be performed by the agent 102 using the current edge data for the edges that are outgoing from the node in the state tree that represents the state characterized by the observation. Selecting an action is described in more detail below with reference to FIG. 3.

Figure 2:
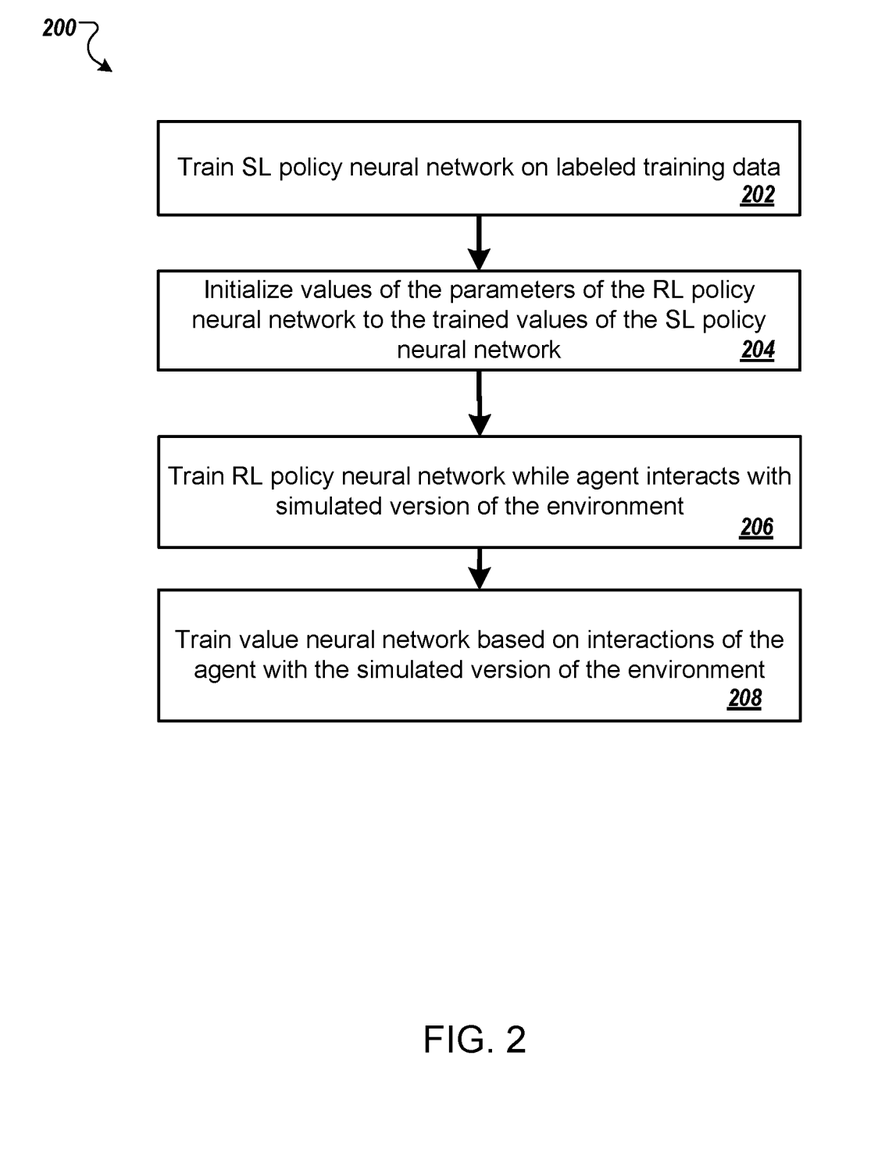
FIG. 2 is a flow diagram of an example process for training a collection of neural networks for use in selecting actions to be performed by an agent interacting with an environment.

FIG. 2 is a flow diagram of an example process 200 for training a collection of neural networks for use in selecting actions to be performed by an agent interacting with an environment. For convenience, the process 200 will be described as being performed by a system of one or more computers located in one or more locations. For example, a reinforcement learning system, e.g., the reinforcement learning system 100 of FIG. 1, appropriately programmed in accordance with this specification, can perform the process 200.

The system trains the SL policy neural network and, when included, the fast rollout policy neural network on labeled training data using supervised learning (step 202).

The labeled training data for the SL policy neural network includes multiple training observations and, for each training observation, an action label that identifies an action that was performed in response to the training observation.

For example, the action labels may identify, for each training observation, an action that was performed by an expert, e.g., an agent being controlled by a human actor, when the environment was in the state characterized by the training observation.

In particular, the system trains the SL policy neural network to generate action probabilities that match the action labels for the labeled training data by adjusting the values of the parameters of the SL policy neural network from initial values of the parameters to trained values of the parameters. For example, the system can train the SL policy neural network using asynchronous stochastic gradient descent updates to maximize the log likelihood of the action identified by the action label for a given training observation.

As described above, the fast rollout policy neural network is a network that generates outputs faster than the SL policy neural network, i.e., because the architecture of the fast rollout policy neural network is more compact than the architecture of the SL policy neural network and the inputs to the fast rollout policy neural network are less complex than the inputs to the SL policy neural network.

Thus, the labeled training data for the fast rollout policy neural network includes training rollout inputs, and for each training rollout input, an action label that identifies an action that was performed in response to the rollout input. For example, the labeled training data for the fast rollout policy neural network may be the same as the labeled training data for the SL policy neural network but with the training observations being replaced with training rollout inputs that characterize the same states as the training observations.

Like the SL policy neural network, the system trains the fast rollout neural network to generate rollout action probabilities that match the action labels in the labeled training data by adjusting the values of the parameters of the fast rollout neural network from initial values of the parameters to trained values of the parameters. For example, the system can train the fast rollout neural network using stochastic gradient descent updates to maximize the log likelihood of the action identified by the action label for a given training rollout input.

The system initializes initial values of the parameters of the RL policy neural network to the trained values of the SL policy neural network (step 204). As described before, the RL policy neural network and the SL policy neural network have the same network architecture, and the system initializes the values of the parameters of the RL policy neural network to match the trained values of the parameters of the SL policy neural network.

The system trains the RL policy neural network while the agent interacts with the simulated version of the environment (step 206).

That is, after initializing the values, the system trains the RL policy neural network to adjust the values of the parameters of the RL policy neural network using reinforcement learning from data generated from interactions of the agent with the simulated version of the environment.

During these interactions, the actions that are performed by the agent are selected using the RL policy neural network in accordance with current values of the parameters of the RL policy neural network.

In particular, the system trains the RL policy neural network to adjust the values of the parameters of the RL policy neural network to generate action probabilities that represent, for each action, the likelihood that for each action, a predicted likelihood that a long-term reward that will be received will be maximized if the action is performed by the agent in response to the observation instead of any other action in the set of possible actions. Generally, the long-term reward is a numeric value that is dependent on the degree to which the one or more objectives are completed during interaction of the agent with the environment.

To train the RL policy neural network, the system completes an episode of interaction of the agent while the actions were being selected using the RL policy neural network and then generates a long-term reward for the episode. The system generates the long-term reward based on the outcome of the episode, i.e., on whether the objectives were completed during the episode. For example, the system can set the reward to one value if the objectives were completed and to another, lower value if the objectives were not completed.

The system then trains the RL policy neural network on the training observations in the episode to adjust the values of the parameters using the long-term reward, e.g., by computing policy gradient updates and adjusting the values of the parameters using those policy gradient updates using a reinforcement learning technique, e.g., REINFORCE.

The system can determine final values of the parameters of the RL policy neural network by repeatedly training the RL policy neural network on episodes of interaction.

The system trains the value neural network on training data generated from interactions of the agent with the simulated version of the environment (step 208).

In particular, the system trains the value neural network to generate a value score for a given state of the environment that represents the predicted long-term reward resulting from the environment being in the state by adjusting the values of the parameters of the value neural network.

The system generates training data for the value neural network from the interaction of the agent with the simulated version of the environment. The interactions can be the same as the interactions used to train the RL policy neural network, or can be interactions during which actions performed by the agent are selected using a different action selection policy, e.g., the SL policy neural network, the RL policy neural network, or another action selection policy.

The training data includes training observations and, for each training observation, the long-term reward that resulted from the training observation.

For example, the system can select one or more observations randomly from each episode of interaction and then associate the observation with the reward for the episode to generate the training data.

As another example, the system can select one or more observations randomly from each episode, simulate the remainder of the episode by selecting actions using one of the policy neural networks, by randomly selecting actions, or both, and then determine the reward for the simulated episode. The system can then randomly select one or more observations from the simulated episode and associate the reward for the simulated episode with the observations to generate the training data.

The system then trains the value neural network on the training observations using supervised learning to determine trained values of the parameters of the value neural network from initial values of the parameters of the neural network. For example, the system can train the value neural network using asynchronous gradient descent to minimize the mean squared error between the value scores and the actual long-term reward received.

Figure 3:
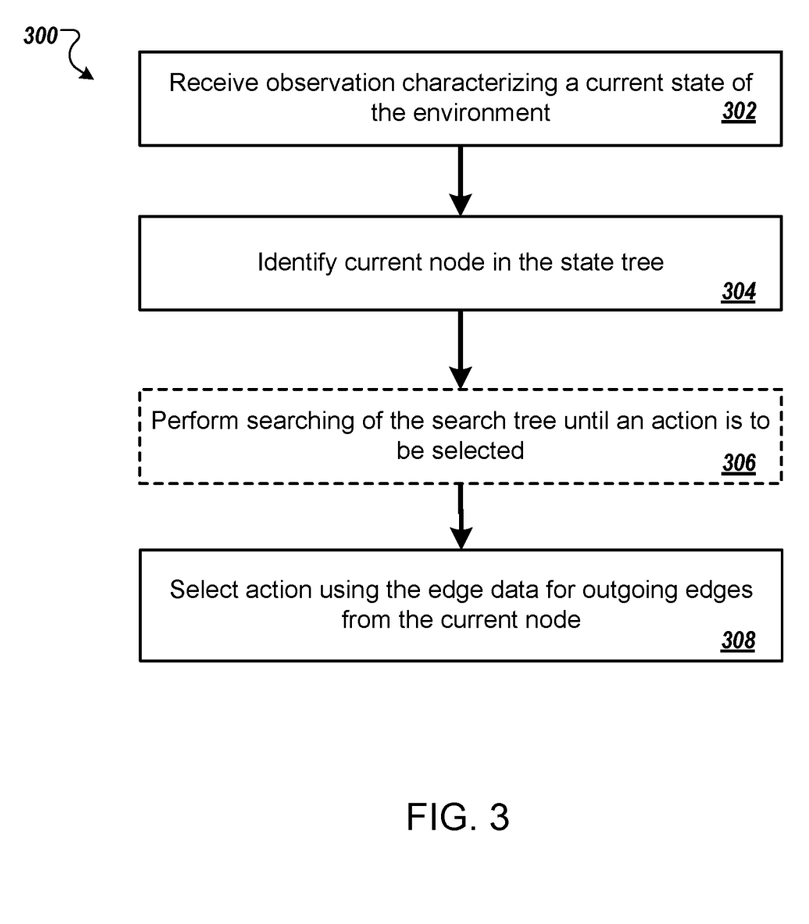
FIG. 3 is a flow diagram of an example process for selecting an action to be performed by the agent using a state tree.

FIG. 3 is a flow diagram of an example process 300 for selecting an action to be performed by the agent using a state tree. For convenience, the process 300 will be described as being performed by a system of one or more computers located in one or more locations. For example, a reinforcement learning system, e.g., the reinforcement learning system 100 of FIG. 1, appropriately programmed in accordance with this specification, can perform the process 300.

The system receives a current observation characterizing a current state of the environment (step 302) and identifies a current node in the state tree that represents the current state (step 304).

Optionally, prior to selecting the action to be performed by the agent in response to the current observation, the system searches or continues to search the state tree until an action is to be selected (step 306). That is, in some implementations, the system is allotted a certain time period after receiving the observation to select an action. In these implementations, the system continues performing searches as described below with reference to FIG. 4, starting from the current node in the state tree until the allotted time period elapses. The system can then update the state tree and the edge data based on the searches before selecting an action in response to the current observation. In some of these implementations, the system searches or continues searching only if the edge data indicates that the action to be selected may be modified as a result of the additional searching.

The system selects an action to be performed by the agent in response to the current observation using the current edge data for outgoing edges from the current node (step 308).

In some implementations, the system selects the action represented by the outgoing edge having the highest action score as the action to be performed by the agent in response to the current observation. In some other implementations, the system selects the action represented by the outgoing edge having the highest visit count as the action to be performed by the agent in response to the current observation.

The system can continue performing the process 300 in response to received observations until the interaction of the agent with the environment terminates. In some implementations, the system continues performing searches of the environment using the simulated version of the environment, e.g., using one or more replicas of the agent to perform the actions to interact with the simulated version, independently from selecting actions to be performed by the agent to interact with the actual environment.

Figure 4:
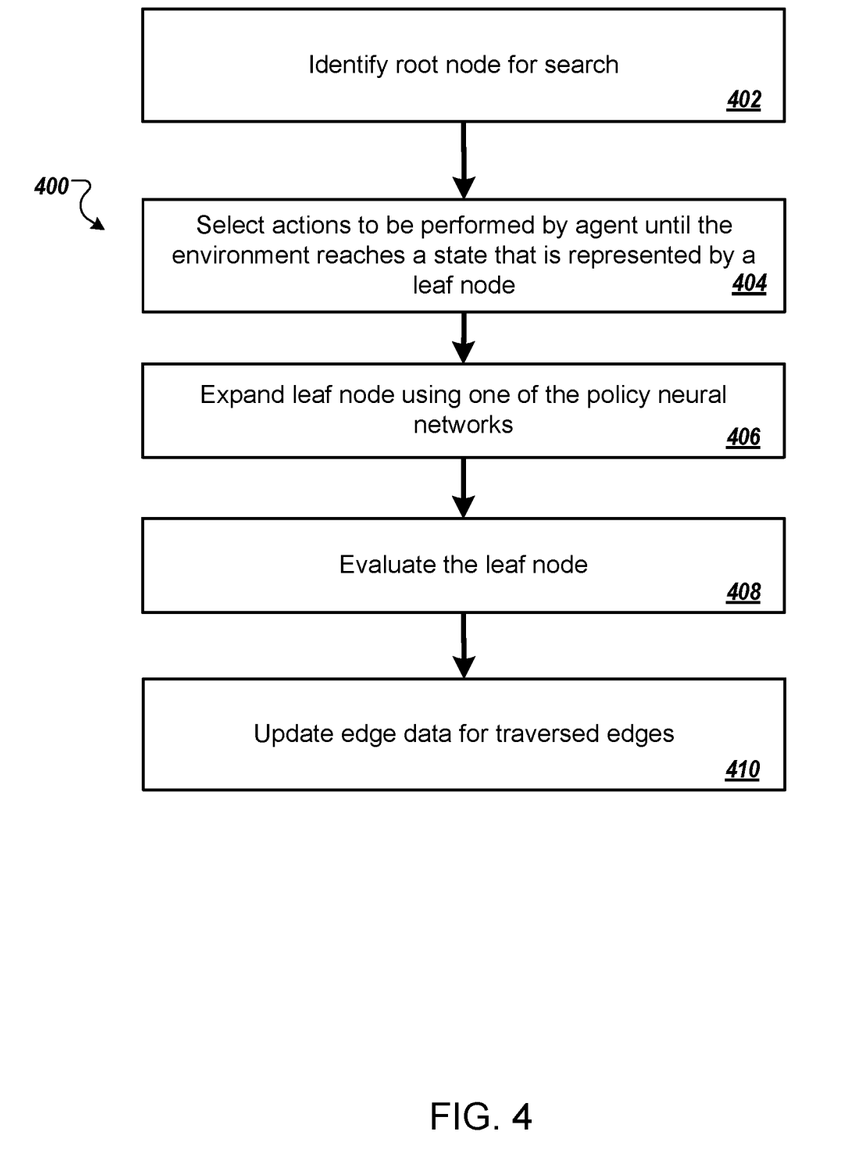
FIG. 4 is a flow diagram of an example process for performing a search of an environment state tree using neural networks.

FIG. 4 is a flow diagram of an example process 400 for performing a search of an environment state tree using neural networks. For convenience, the process 400 will be described as being performed by a system of one or more computers located in one or more locations. For example, a reinforcement learning system, e.g., the reinforcement learning system 100 of FIG. 1, appropriately programmed in accordance with this specification, can perform the process 400.

The system receives data identifying a root node for the search, i.e., a node representing an initial state of the simulated version of the environment (step 402).

The system selects actions to be performed by the agent to interact with the environment by traversing the state tree until the environment reaches a leaf state, i.e., a state that is represented by a leaf node in the state tree (step 404).

That is, in response to each received observation characterizing an in-tree state, i.e., a state encountered by the agent starting from the initial state until the environment reaches the leaf state, the system selects an action to be performed by the agent in response to the observation using the edge data for the outgoing nodes from the in-tree node representing the in-tree state.

In particular, for each outgoing edge from an in-tree node, the system determines an adjusted action score for the edge based on the action score for the edge, the visit count for the edge, and the prior probability for the edge. Generally, the system computes the adjusted action score for a given edge by adding to the action score for the edge a bonus that is proportional to the prior probability for the edge but decays with repeated visits to encourage exploration. For example, the bonus may be directly proportional to a ratio that has the prior probability as the numerator and a constant, e.g., one, plus the visit count as the denominator.

The system then selects the action represented by the edge with the highest adjusted action score as the action to be performed by the agent in response to the observation.

The system continues selecting actions to be performed by the agent in this manner until an observation is received that characterizes a leaf state that is represented by a leaf node in the state tree. Generally, a leaf node is a node in the state tree that has no child nodes, i.e., is not connected to any other nodes by an outgoing edge.

The system expands the leaf node using one of the policy neural networks (step 406). That is, in some implementations, the system uses the SL policy neural network in expanding the leaf node, while in other implementations, the system uses the RL policy neural network.

To expand the leaf node, the system adds a respective new edge to the state tree for each action that is a valid action to be performed by the agent in response to the leaf observation. The system also initializes the edge data for each new edge by setting the visit count and action scores for the new edge to zero. To determine the prior probability for each new edge, the system processes the leaf observation using the policy neural network, i.e., either the SL policy neural network or the RL policy neural network depending on the implementation, and uses the action probabilities generated by the network as the prior probabilities for the corresponding edges. In some implementations, the temperature of the output layer of the policy neural network is reduced when generating the prior probabilities to smooth out the probability distribution defined by the action probabilities.

The system evaluates the leaf node using the value neural network and, optionally, the fast rollout policy neural network to generate a leaf evaluation score for the leaf node (step 408).

To evaluate the leaf node using the value neural network, the system processes the observation characterizing the leaf state using the value neural network to generate a value score for the leaf state that represents a predicted long-term reward received as a result of the environment being in the leaf state.

To evaluate the leaf node using the fast rollout policy neural network, the system performs a rollout until the environment reaches a terminal state by selecting actions to be performed by the agent using the fast rollout policy neural network. That is, for each state encountered by the agent during the rollout, the system receives rollout data characterizing the state and processes the rollout data using the fast rollout policy neural network that has been trained to receive the rollout data to generate a respective rollout action probability for each action in the set of possible actions. In some implementations, the system then selects the action having a highest rollout action probability as the action to be performed by the agent in response to the rollout data characterizing the state. In some other implementations, the system samples from the possible actions in accordance with the rollout action probabilities to select the action to be performed by the agent.

The terminal state is a state in which the objectives have been completed or a state which has been classified as a state from which the objectives cannot be reasonably completed. Once the environment reaches the terminal state, the system determines a rollout long-term reward based on the terminal state. For example, the system can set the rollout long-term reward to a first value if the objective was completed in the terminal state and a second, lower value if the objective is not completed as of the terminal state.

The system then either uses the value score as the leaf evaluation score for the leaf node or if, both the value neural network and the fast rollout policy neural network are used, combines the value score and the rollout long-term reward to determine the leaf evaluation score for the leaf node. For example, when combined, the leaf evaluation score can be a weighted sum of the value score and the rollout long-term reward.

The system updates the edge data for the edges traversed during the search based on the leaf evaluation score for the leaf node (step 410).

In particular, for each edge that was traversed during the search, the system increments the visit count for the edge by a predetermined constant value, e.g., by one. The system also updates the action score for the edge using the leaf evaluation score by setting the action score equal to the new average of the leaf evaluation scores of all searches that involved traversing the edge.

While the description of FIG. 4 describes actions being selected for the agent interacting with the environment, it will be understood that the process 400 may instead be performed to search the state tree using the simulated version of the environment, i.e., with actions being selected to be performed by the agent or a replica of the agent to interact with the simulated version of the environment.

In some implementations, the system distributes the searching of the state tree, i.e., by running multiple different searches in parallel on multiple different machines, i.e., computing devices.

For example, the system may implement an architecture that includes a master machine that executes the main search, many remote worker CPUs that execute asynchronous rollouts, and many remote worker GPUs that execute asynchronous policy and value network evaluations. The entire state tree may be stored on the master, which only executes the in-tree phase of each simulation. The leaf positions are communicated to the worker CPUs, which execute the rollout phase of simulation, and to the worker GPUs, which compute network features and evaluate the policy and value networks.

In some cases, the system does not update the edge data until a predetermined number of searches have been performed since a most-recent update of the edge data, e.g., to improve the stability of the search process in cases where multiple different searches are being performed in parallel.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a relationship graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A system comprising one or more computers and one or more storage devices storing instructions that when executed by the one or more computers cause the one or more computers to perform operations comprising:
    maintaining data representing a state tree of an environment being interacted with by an agent by performing actions selected from a set of actions,
        wherein the state tree comprises a plurality of nodes and a plurality of edges,
        wherein each node represents a respective state of the environment that has been encountered by the agent during interaction with the environment or with a simulated version of the environment, and
        wherein each edge connects a respective first node to a respective second node and represents an action that (i) was performed by the agent in response to an observation characterizing a first state represented by the respective first node and (ii) resulted in the environment or the simulated version of the environment transitioning into a second state represented by the respective second node;
    maintaining edge data, the edge data comprising, for each of the plurality of edges:
        (i) a respective action score for the action represented by the edge,
        (ii) a respective visit count that represents a number of times that the action represented by the edge has been performed by the agent in response to observations characterizing the respective first state represented by the respective first node for the edge, and
        (iii) a respective prior probability, wherein the respective prior probability for each of the edges represents a likelihood that the action represented by the edge is an action that should be performed in response to the observations characterizing the respective first state as determined by an output of a policy neural network;
    receiving a root observation characterizing a root state of the environment that is represented by a root node of the plurality of nodes;
    selecting actions to be performed by the agent to interact with the environment or the simulated version of the environment by traversing the state tree from the root node according to the edge data until the environment or the simulated version of the environment reaches a leaf state represented by a leaf node in the state tree, wherein traversing the state tree comprises:
        receiving an observation characterizing an in-tree state that is represented by an in-tree node that is between the root node and the leaf node; and
        selecting, from the actions represented by the edges from the in-tree node to respective other nodes, an action to be performed by the agent in response to the observation characterizing the in-tree state using at least the action scores for the edges and the prior probabilities for the edges from the in-tree node;
    evaluating the leaf node by processing a leaf observation characterizing the leaf node using a value neural network that has been trained to process the leaf observation to generate a value score for the leaf state that represents a predicted long-term reward received as a result of the environment being in the leaf state, wherein the value neural network comprises a regression output layer that outputs the value score; and updating the edge data for edges traversed during the traversal, comprising: updating the action score for each edge based at least on the value score for the leaf state generated by the value neural network.

2. The system of claim 1,
wherein the environment is a real-world environment, and
wherein the actions in the set of actions are control inputs to control the interaction of the agent with the environment.

3. The system of claim 2,
wherein the environment is a real-world environment,
wherein the agent is a control system for an autonomous or semi-autonomous vehicle navigating through the real-world environment, and
wherein the actions in the set of actions are control inputs to control the autonomous or semi-autonomous vehicle.

4. The system of claim 3,
wherein the predicted long-term reward received by the agent reflects a predicted degree to which objectives for the navigation of the vehicle through the real-world environment will be satisfied as a result of the environment being in the leaf state.

5. The system of claim 1,
wherein the environment is a patient diagnosis environment,
wherein each state is a respective patient state of a patient,
wherein the agent is a computer system for suggesting treatment for the patient, and
wherein the actions in the set of actions are medical treatments.

6. The system of claim 1,
wherein the environment is a protein folding environment,
wherein each state is a respective state of a protein chain,
wherein the agent is a computer system for determining how to fold the protein chain, and
wherein the actions are folding actions for folding the protein chain.

7. The system of claim 1,
wherein the environment is a virtual environment in which a user competes against a computerized agent to accomplish a goal,
wherein the agent is the computerized agent, and
wherein the actions in the set of actions are actions that can be performed by the computerized agent.

8. The system of claim 1, the operations further comprising:
evaluating the leaf node by performing a rollout until the environment or the simulated version of the environment reaches a terminal state, comprising:
for each state encountered by the agent during the rollout:
receiving rollout data characterizing the state;
processing the rollout data using a fast rollout policy neural network that has been trained to receive the rollout data and to process the rollout data to generate a respective rollout action probability for each action in the set of actions; and
selecting an action as an action to be performed by the agent in response to the rollout data characterizing the state using the respective rollout action probabilities; and generating a rollout long-term reward based on the terminal state.

9. The system of claim 8, wherein updating the edge data comprises:
generating a leaf evaluation score by combining the rollout long-term reward and the value score generated by the value neural network; and
updating the action score for each edge traversed during the traversal based on the leaf evaluation score.

10. The system of claim 9, wherein updating the edge data comprises, for each edge that was traversed:
incrementing the visit count for the edge; and
updating the action score for the edge using the leaf evaluation score such that the action score is an average of leaf evaluation scores for each time the edge has been traversed.

11. The system of claim 10, the operations further comprising:
adding a respective new edge to the state tree for each action that is a valid action to be performed by the agent in response to the leaf observation.

12. The system of claim 11, the operations further comprising:
generating edge data for each new edge, comprising generating a prior probability for the new edge by processing the leaf observation using a policy neural network, wherein the policy neural network is configured to process the leaf observation to generate a respective action probability for each action in the set of actions.

13. The system of claim 12, wherein the policy neural network has been trained using supervised learning.

14. The system of claim 12, wherein the policy neural network has been trained using reinforcement learning.

15. The system of claim 1, wherein selecting, from the actions represented by the edges from the in-tree node to respective other nodes, an action to be performed by the agent in response to the observation characterizing the in-tree state comprises:
determining, for each edge from the in-tree node to another node, an adjusted action score for the edge based on the action score for the edge, the visit count for the edge, and the prior probability for the edge; and
selecting an action represented by an edge having a highest adjusted action score as the action to be performed by the agent in response to the observation characterizing the in-tree state.

16. The system of claim 15, wherein the adjusted action score for each edge is the action score for each edge plus a bonus that is proportional to the prior probability for the edge but decays with repeated visits to encourage exploration.

17. The system of claim 1, the operations further comprising:
receiving a current observation characterizing a current state of the environment;
identifying a current node representing the current state; and
selecting an action to be performed by the agent from edge data for outgoing edges from the current node.

18. The system of claim 17, wherein selecting an action to be performed by the agent from edge data for outgoing edges from the current node comprises:
selecting the action from the actions represented by outgoing edges from the current node that has the highest visit count.

19. The system of claim 17, wherein selecting an action to be performed by the agent from edge data for outgoing edges from the current node comprises:
  selecting the action from the actions represented by outgoing edges from the current node that has the highest action score.

20. A method comprising:
  maintaining data representing a state tree of an environment being interacted with by an agent by performing actions selected from a set of actions,
    wherein the state tree comprises a plurality of nodes and a plurality of edges,
    wherein each node represents a respective state of the environment that has been encountered by the agent during interaction with the environment or with a simulated version of the environment, and
    wherein each edge connects a respective first node to a respective second node and represents an action that (i) was performed by the agent in response to an observation characterizing a first state represented by the respective first node and (ii) resulted in the environment or the simulated version of the environment transitioning into a second state represented by the respective second node;
  maintaining edge data, the edge data comprising, for each of the plurality of edges:
    (i) a respective action score for the action represented by the edge,
    (ii) a respective visit count that represents a number of times that the action represented by the edge has been performed by the agent in response to observations characterizing the respective first state represented by the respective first node for the edge, and
    (iii) a respective prior probability, wherein the respective prior probability for each of the edges represents a likelihood that the action represented by the edge is an action that should be performed in response to the observations characterizing the respective first state as determined by an output of a policy neural network;
  receiving a root observation characterizing a root state of the environment that is represented by a root node of the plurality of nodes;
  selecting actions to be performed by the agent to interact with the environment or the simulated version of the environment by traversing the state tree from the root node according to the edge data until the environment or the simulated version of the environment reaches a leaf state represented by a leaf node in the state tree, wherein traversing the state tree comprises:
    receiving an observation characterizing an in-tree state that is represented by an in-tree node that is between the root node and the leaf node; and
    selecting, from the actions represented by the edges from the in-tree node to respective other nodes, an action to be performed by the agent in response to the observation characterizing the in-tree state using at least the action scores for the edges and the prior probabilities for the edges from the in-tree node;
  evaluating the leaf node by processing a leaf observation characterizing the leaf node using a value neural network that has been trained to process the leaf observation to generate a value score for the leaf state that represents a predicted long-term reward received as a result of the environment being in the leaf state, wherein the value neural network comprises a regression output layer that outputs the value score; and
  updating the edge data for edges traversed during the traversal, comprising: updating the action score for each edge based at least on the value score for the leaf state generated by the value neural network.

21. One or more non-transitory storage media storing instructions that when executed by one or more computers cause the one or more computers to perform operations comprising:
  maintaining data representing a state tree of an environment being interacted with by an agent by performing actions selected from a set of actions,
    wherein the state tree comprises a plurality of nodes and a plurality of edges,
    wherein each node represents a respective state of the environment that has been encountered by the agent during interaction with the environment or with a simulated version of the environment, and
    wherein each edge connects a respective first node to a respective second node and represents an action that (i) was performed by the agent in response to an observation characterizing a first state represented by the respective first node and (ii) resulted in the environment or the simulated version of the environment transitioning into a second state represented by the respective second node;
  maintaining edge data, the edge data comprising, for each of the plurality of edges:
    (i) a respective action score for the action represented by the edge,
    (ii) a respective visit count that represents a number of times that the action represented by the edge has been performed by the agent in response to observations characterizing the respective first state represented by the respective first node for the edge, and
    (iii) a respective prior probability, wherein the respective prior probability for each of the edges represents a likelihood that the action represented by the edge is an action that should be performed in response to the observations characterizing the respective first state as determined by an output of a policy neural network;
  receiving a root observation characterizing a root state of the environment that is represented by a root node of the plurality of nodes;
  selecting actions to be performed by the agent to interact with the environment or the simulated version of the environment by traversing the state tree from the root node according to the edge data until the environment or the simulated version of the environment reaches a leaf state represented by a leaf node in the state tree, wherein traversing the state tree comprises:
    receiving an observation characterizing an in-tree state that is represented by an in-tree node that is between the root node and the leaf node; and
    selecting, from the actions represented by the edges from the in-tree node to respective other nodes, an action to be performed by the agent in response to the observation characterizing the in-tree state using at least the action scores for the edges and the prior probabilities for the edges from the in-tree node;
  evaluating the leaf node by processing a leaf observation characterizing the leaf node using a value neural network that has been trained to process the leaf observation to generate a value score for the leaf state that represents a predicted long-term reward received as a result of the environment being in the leaf state, wherein the value neural network comprises a regression output layer that outputs the value score; and updating the edge data for edges traversed during the traversal, comprising: updating the action score for each edge based at least on the value score for the leaf state generated by the value neural network.

\* \* \* \* \*

UNITED STATES PATENT AND TRADEMARK OFFICE
CERTIFICATE OF CORRECTION

| | | |
|---|---|---|
| PATENT NO. | : 10,867,242 B2 | Page 1 of 1 |
| APPLICATION NO. | : 15/280784 | |
| DATED | : December 15, 2020 | |
| INVENTOR(S) | : Graepel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 712 days.

Signed and Sealed this
Sixth Day of December, 2022

*Katherine Kelly Vidal*

Katherine Kelly Vidal
*Director of the United States Patent and Trademark Office*